United States Patent
Azimi et al.

(10) Patent No.: US 7,701,571 B2
(45) Date of Patent: Apr. 20, 2010

(54) RAMAN SPECTROMETRY ASSEMBLY

(75) Inventors: Masud Azimi, Belmont, MA (US); Kevin J. Knopp, Newburyport, MA (US); Steve McLaughlin, Andover, MA (US)

(73) Assignee: Ahura Scientific Inc., Wilmington, MA (US)

( * ) Notice: Subject to any disclaimer, the term of this patent is extended or adjusted under 35 U.S.C. 154(b) by 172 days.

(21) Appl. No.: 11/894,887

(22) Filed: Aug. 22, 2007

(65) Prior Publication Data

US 2009/0033928 A1 Feb. 5, 2009

Related U.S. Application Data

(60) Provisional application No. 60/839,188, filed on Aug. 22, 2006.

(51) Int. Cl.
*G01J 3/44* (2006.01)
*G01N 21/65* (2006.01)

(52) U.S. Cl. .................................... 356/301
(58) Field of Classification Search .................. 356/301
See application file for complete search history.

(56) References Cited

U.S. PATENT DOCUMENTS

| | | | |
|---|---|---|---|
| 3,017,513 A | 1/1962 | Messelt | |
| 3,906,241 A | 9/1975 | Thompson | |
| 5,026,160 A | 6/1991 | Dorain et al. | |
| 5,048,959 A | 9/1991 | Morris et al. | |
| 5,436,454 A * | 7/1995 | Bornstein et al. | ...... 250/339.12 |
| 5,483,337 A | 1/1996 | Barnard et al. | |
| 5,651,018 A | 7/1997 | Mehuys et al. | |
| 5,734,165 A | 3/1998 | Unal et al. | |
| 5,828,450 A | 10/1998 | Dou et al. | |
| 5,862,273 A * | 1/1999 | Pelletier | ...................... 356/301 |
| 6,069,689 A | 5/2000 | Zeng et al. | |
| 6,249,349 B1 | 6/2001 | Lauer | |
| 6,303,934 B1 | 10/2001 | Daly et al. | |
| 6,608,677 B1 | 8/2003 | Ray et al. | |
| 6,802,653 B2 * | 10/2004 | Deane | ........................ 385/88 |
| 6,803,328 B2 | 10/2004 | McCullough | |
| 6,862,092 B1 | 3/2005 | Ibsen et al. | |
| 6,977,723 B2 | 12/2005 | Lemmo et al. | |
| 2002/0033944 A1 | 3/2002 | Sharts et al. | |
| 2003/0002548 A1 | 1/2003 | Boscha | |
| 2003/0002839 A1 | 1/2003 | Clow et al. | |
| 2003/0085348 A1 | 5/2003 | Megerle | |

(Continued)

OTHER PUBLICATIONS

Eckenrode, Brian A. et al., Portable Raman Spectroscopy Systems for Field Analysis, Forensic Science Communications, Oct. 2001, vol. 3, No. 4.

(Continued)

*Primary Examiner*—F. L Evans
(74) *Attorney, Agent, or Firm*—Fish & Richardson P.C.

(57) ABSTRACT

A Raman spectrometry assembly includes a Raman spectrometer having a laser light source and a Raman signal analyzer, an interface module comprising a housing which is connectable to and disconnectable from the spectrometer, and a fiber optic assembly which is connectable to and disconnectable from the interface module, the fiber optic assembly including optical fibers and a probe head at a distal end thereof for disposition adjacent a specimen to be tested, the optical fibers extending from the probe head and adapted to extend to the interface module.

23 Claims, 4 Drawing Sheets

U.S. PATENT DOCUMENTS

| | | |
|---|---|---|
| 2003/0197860 A1 | 10/2003 | Rice |
| 2004/0039274 A1 | 2/2004 | Benaron et al. |
| 2004/0109230 A1 | 6/2004 | Matsushita et al. |
| 2004/0165183 A1 | 8/2004 | Marquardt et al. |
| 2004/0165254 A1 | 8/2004 | Tokura et al. |
| 2004/0252299 A9 | 12/2004 | Lemmo et al. |
| 2004/0263843 A1 | 12/2004 | Knopp et al. |
| 2005/0083521 A1 | 4/2005 | Kamerman |
| 2006/0023209 A1 | 2/2006 | Lee et al. |
| 2006/0170917 A1 | 8/2006 | Vakhshoori et al. |
| 2006/0262300 A1* | 11/2006 | Gylys et al. .............. 356/301 |

OTHER PUBLICATIONS

Harvey, S.D. et al., Blind field test evaluation of Raman spectroscopy as a forensic tool, Forensic Science International, 2002, 12-21, 125.

Moore, D.S., Instrumentation for trace detection of high explosives, Aug. 2004, 2499-2512, vol. 75, No. 8.

* cited by examiner

RAMAN SPECTROMETRY ASSEMBLY

REFERENCE TO PENDING PRIOR PATENT APPLICATION

This patent application claims the benefit of U.S. Provisional Patent Application Ser. No. 60/839,188 filed Aug. 22, 2006, in the names of Masud Azimi, Kevin Knopp and Steve Mclaughlin.

BACKGROUND OF THE INVENTION

1. Field of the Invention

This invention relates to apparatus for identifying and characterizing substances using Raman spectroscopy, which provides a non-contact and non-invasive technique for investigation and analysis of chemical substances.

2. Description of the Prior Art

Raman spectroscopy is widely used in the scientific, commercial and public safety areas.

Technological advances are making it possible to increase the range of applications using Raman spectroscopy, through reductions in costs and size of the equipment. Portable units have become available for field uses, such as on-site identification of potentially hazardous materials.

In applications of Raman spectroscopy, it is generally desirable to bring an optical probe to a position adjacent a specimen. This can be a problem in view of the potentially hazardous materials which are to be analyzed, including explosives, chemical agents, toxic industrial chemicals, and the like. In some applications, it is required, for safety reasons, that delivery of laser light to a specimen under test, and a collection of Raman signal from the specimen, be done at a location remote from the Raman spectrometer hardware. Optical fiber, which can serve as a conduit for laser light and Raman signal light, is a good medium for achieving this. However, there are some problems in the use of optical fibers and probes for Raman spectroscopy.

Firstly, the distal end of the probe can become contaminated during data collection and it is often desirable, and at times necessary, to replace the probe head, which is very costly, if it can be done at all. Accordingly, there is a need for a relatively inexpensive optical fiber assembly, including optical fiber and a probe head, which can be disconnected from the spectrometer and replaced with another optical fiber assembly.

Secondly, propagation of a high power laser light within an optical fiber generates unwanted Raman signal from the optical fiber material itself which adds to the Raman signal collected from a specimen and, in many cases, is difficult to distinguish from the specimen signal and difficult to subtract from the Raman signal generated from the specimen under test.

Accordingly, there is a further need for means for preventing Raman signals generated by the material of an excitation fiber of an optical fiber assembly from reaching the specimen under test, such that only the excitation laser signal reaches the specimen and the Raman signals received from the specimen and conducted to a spectrometer by way of a collection fiber of the optical fiber assembly are from the specimen only and not from the excitation fiber.

Thirdly, the laser light exiting the distal end of the excitation fiber diverges immediately and does so until the excitation light reaches the specimen under test. Thus, the portion of the excitation light which reaches the specimen reduces, increasingly, as the distance between the excitation fiber and the specimen increases.

There is accordingly a still further need for means to focus the light from the excitation fiber onto a small area of the specimen. Similarly, Raman signals reflected off the specimen diverge outwardly from the specimen with only a small portion of the reflected light reaching an end of a collection fiber. Accordingly, there is also a need for means to focus Raman light from a specimen onto the small area of an end of a collection fiber.

SUMMARY OF THE INVENTION

Accordingly, an object of the invention is to provide a Raman Spectrometry Assembly in which a fiber optic assembly, including a probe head and optical fibers, is detachable from a Raman spectrometer and readily replaced with the same or another fiber optic assembly.

A further object of the invention is to provide such a fiber optic assembly in which the laser light from the spectrometer carried by the excitation fiber does not interfere with Raman signal generated by the material of the excitation fiber, such that substantially only the excitation laser impinges upon the specimen and the Raman signal reflected therefrom includes only Raman signal from the specimen.

A still further object of the invention is to provide such a fiber optic assembly in which laser light emanating from the excitation fiber distal end is focused on a small portion of the sample under test, and diverging Raman signal light reflected off the sample is focused so as to enter an end of the collection fiber for transmission to the Raman signal analyzer.

With the above and other objects in view, a feature of the present invention is the provision of a Raman spectrometry assembly, the assembly including a Raman spectrometer comprising a laser light source and a Raman signal analyzer, an interface module comprising a housing which is attachable to and detachable from the spectrometer, and a fiber optic assembly which is attachable to and detachable from the interface module, the fiber optic assembly comprising a probe head portion at a distal end thereof for disposition adjacent a specimen to be tested, and optical fibers extending from the probe head and adapted to extend to the interface module.

In accordance with a further feature of the invention, there is provided a Raman spectrometer assembly, the assembly including a Raman spectrometer comprising a laser light source and a Raman signal analyzer, a housing for releasable connection to the spectrometer, and having first and second openings extending through a wall thereof, first and second sleeves disposed in the first and second openings, a fiber optic assembly comprising first and second ferrules adapted for insertion into and withdrawal from the sleeves, an elongated excitation fiber fixed to and extending from the first ferrule and an elongated collection fiber fixed to and extending from the second ferrule, distal ends of the fibers being fixed in a probe head portion of the fiber optic assembly, and light manipulating components disposed in the housing and adapted to guide laser light to the first ferrule and thence to the excitation fiber, and to guide Raman signature light from a specimen under test to the second ferrule and thence to the Raman signal analyzer, wherein the ferrules are readily withdrawable from the sleeves and replaceable therein or by other ferrules.

In accordance with a still further feature of the invention, there is provided a Raman spectrometry assembly, the assembly including a Raman spectrometer comprising a laser light source and a Raman signal analyzer, an interface module adapted for connection to and disconnection from the spectrometer, and having a first opening extending through a wall thereof, light manipulating components disposed in the interface module for directing a laser beam emitted from the laser light source of the spectrometer toward the first opening, a first focusing lens mounted in the interface module and aligned with the first opening, and a first sleeve disposed in the first opening. The spectrometer assembly further includes a fiber optic assembly comprising a first ferrule adapted for insertion into the first sleeve and adapted for removal therefrom, the first ferrule being further adapted to reside in the sleeve and therein to receive and transmit the laser light emitted from the laser light source and the laser light directing components to an excitation fiber proximal end fixed to the first ferrule, an elongated excitation fiber extending from the proximal end thereof fixed in the first ferrule to a distal end thereof fixed in a portion of a probe head, a collection fiber extending from the probe head to a second ferrule which is removably disposed in a second sleeve disposed in a second opening in a wall of the interface module. The interface module further comprises a second focusing lens aligned with the second opening and adapted to pass collection fiber light therethrough and toward a portion of the light directing components to the Raman signal analyzer of the spectrometer. The ferrules are removable from the sleeves, and the sleeves are adapted to receive further ferrules of a configuration substantially identical to the first ferrule and the second ferrule, wherein the fiber optic assembly may readily be replaced by another fiber optic assembly.

In accordance with a still further feature of the invention, there is provided a Raman spectrometry assembly, the assembly including a Raman spectrometer comprising a laser light source and a Raman signal analyzer, an interface module adapted to pass laser light therethrough and into a flexible excitation fiber connected to the module, and adapted to pass Raman signal light from a flexible collection fiber connected to the interface module therethrough to the Raman signal analyzer, and a fiber optic assembly comprising the excitation fiber and the collection fiber, a flexible elongated protective shielding disposed around the excitation fiber and the collection fiber, and a probe head at a distal end thereof for disposition adjacent a sample to be tested, the excitation and collection fibers being adapted to extend from the probe head to the interface module, and a band pass filter at the distal end of the excitation fiber to prevent passage of laser light therethrough, but block passage of Raman signal light in the excitation fiber derived from the excitation fiber, such that the Raman signal light generated in the excitation fiber is prevented from reaching the sample.

In accordance with a still further feature of the invention, there is provided a Raman spectrometry assembly, the assembly including a Raman spectrometer comprising a laser light source and a Raman signal analyzer, an interface module comprising a housing which is connectable to and disconnectable from the spectrometer, and a fiber optic assembly which is connectable to and disconnectable from the interface module, the fiber optic assembly comprising a probe head portion at a distal end thereof for disposition adjacent a specimen to be tested, and optical fibers extending from the probe head and adapted to extend to the interface module, the optical fibers including an excitation fiber for transmitting laser light from the interface module to a specimen under test, and a collection fiber for transmitting Raman signal light from the specimen to the interface module, and a lens aligned distally of the distal ends of the optical fibers, the lens being adapted to intercept diverging laser light emanating from the excitation fiber and focus the laser light on a reduced area of the specimen, and to intercept a Raman signal light reflected from the specimen and focus the Raman signal light onto the distal end of the collection fiber.

In accordance with a still further feature of the invention, there is provided a method for obtaining an analysis of a specimen, the method comprising the steps of providing a Raman spectrometer having a laser light source and a Raman signal analyzer, providing an interface module which is adapted for attachment to the spectrometer, the module having therein light manipulating devices for directing laser light and Raman signal light for effecting excitation of the specimen and collection and directing of Raman signal light to the Raman signal analyzer, and providing a fiber optic assembly comprising an excitation fiber, a collection fiber, and a probe head, attaching the interface module to the spectrometer, attaching the fiber optic assembly to the interface module, placing the probe head adjacent the specimen, and energizing the laser light source, whereby to cause laser light to pass from the spectrometer to the interface module and therein to be directed by the light manipulating devices to the excitation fiber and the probe head and onto the specimen, and thence to pass Raman signal light back through the collection fiber to the interface module wherein the manipulating devices direct the Raman signal light to the spectrometer Raman light analyzer.

In accordance with a still further feature of the invention, there is provided a Raman spectrometry assembly including a Raman spectrometer comprising a laser light source and a Raman signal analyzer, an interface module, and a fiber optic assembly connectable to and disconnectable from the interface module. The fiber optic assembly includes a probe head at a distal end thereof for disposition adjacent a specimen to be tested, and optical fibers extending from the probe head and adapted to extend to the interface module. The optical fibers include an excitation fiber for transmitting laser light from the interface module to a specimen under test, and a collection fiber for transmitting Raman signal light from the specimen to said interface module. The probe head assembly includes first and second lenses aligned distally of distal ends of the optical fibers, the first lens being adapted to intercept diverging laser light emanating from the excitation fiber and collimate the laser light, and the second lens being adapted to intercept a Raman signal light reflected from the specimen and focus the Raman signal light onto a distal end of the collection fiber. The assembly further includes a band pass filter at the distal end of the probe head and adapted to suppress Raman signal generated by excitation fiber material and prevent such signal from reaching the specimen, a reflector for redirecting filtered laser light to a notch filter, wherein the notch filter is disposed in the probe head and is adapted to transmit Raman signal light emanating from the specimen and to block laser light reflected back from the specimen from reaching the distal end of the collection fiber, and a focusing lens disposed at the distal end of the probe head, and adapted to focus the laser light on a reduced area of the specimen, and further adapted to collect Raman signal light generated and reflected from the sample and direct the reflected light toward the distal end of the collection fiber. The assembly still further includes a water-sealed enclosure made of a selected one of metal, plastic, ceramic material and any chemically inert material, to house components of the probe head assembly.

The above and other features of the invention, including various novel details of construction and combinations of parts and method steps, will now be more particularly described with reference to the accompanying drawings and pointed out in the claims. It will be understood that the particular devices and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention from which its novel features and advantages will be apparent.

In the drawings.

DESCRIPTION OF THE PREFERRED EMBODIMENTS

Figure 1:
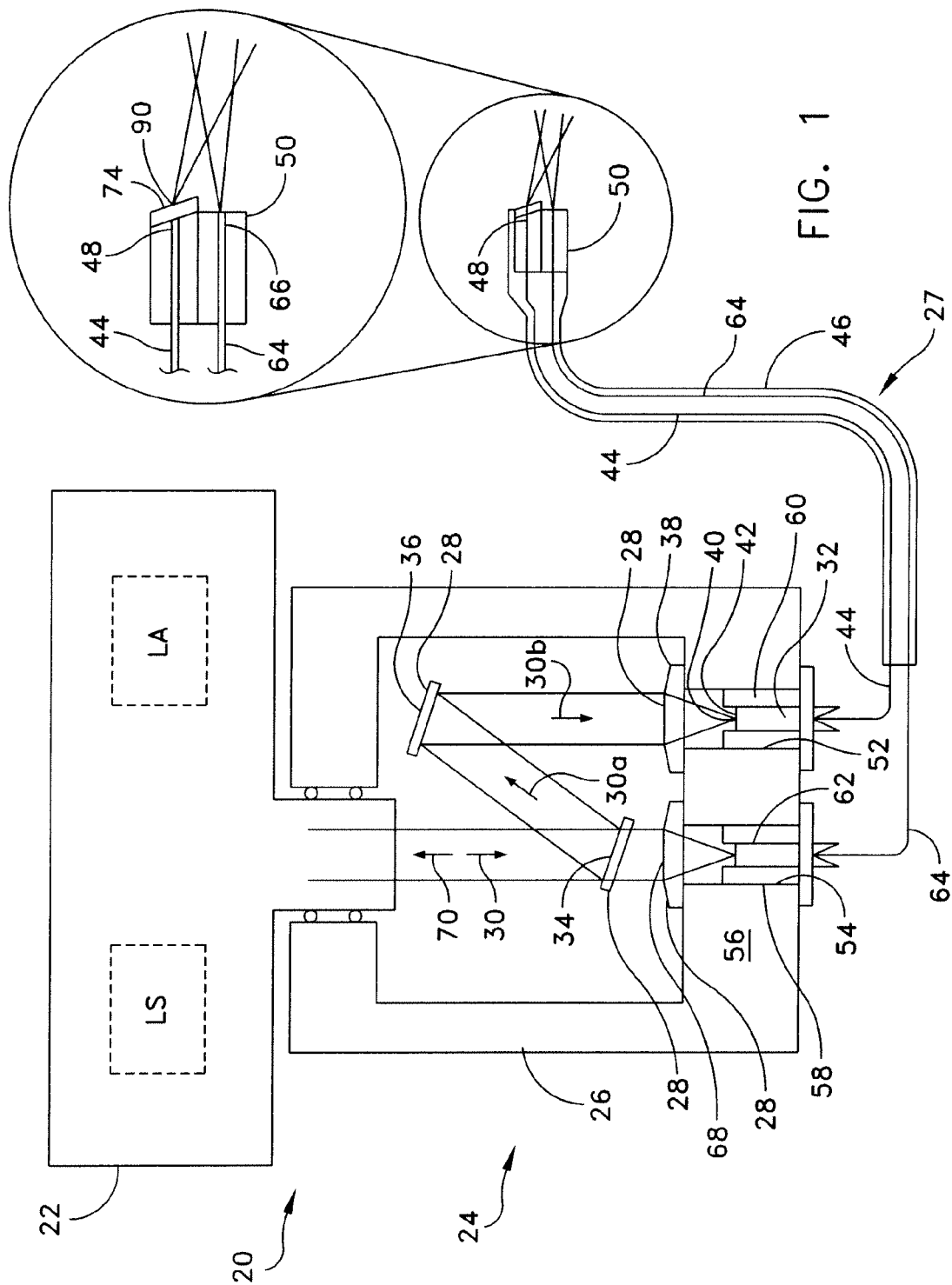
FIG. 1 is a schematic illustration of one form of spectrometry assembly illustrative of an embodiment of the invention.

Referring to FIG. 1, it will be seen that an illustrative Raman spectroscopy assembly 20 includes a Raman spectrometer 22 including a laser light source LS and a light analyzer LA, as is known in the art.

The assembly 20 further includes an interface module 24 comprising a housing 26 which is connectable to, and disconnectable from, the spectrometer 22, and a fiber optic assembly 27 which is connectable to, and disconnectable from, the interface module 24.

Mounted in the housing 26 are light manipulating devices 28 arranged so as to receive laser light 30 from the spectrometer 22 and direct the laser light, finely focused, to a first ferrule 32 of the fiber optic assembly 27. The light manipulating devices 28 are further arranged to receive Raman signal light and direct the Raman signal light to the light analyzer LA of the spectrometer 22.

In the embodiment shown in FIG. 1, the particular light manipulating devices 28 include a notch filter 34 which directs laser light 30a toward a reflector 36 which directs the laser light 30b through a focusing lens 38 which focuses the light 30b onto a fine point 40 on an inner end 42 of the ferrule 32.

In the fiber optic assembly 27, ferrule 32 has fixed thereto a flexible excitation fiber 44 housed in a flexible protective shielding 46. A distal end 48 of the laser fiber 44 is held in a probe head 50.

The housing 26 is provided with two openings 52, 54 extending through a wall 56 thereof. Flanged sleeves 60, 58 are fixed in openings 52, 54, respectively. The ferrule 32 of the fiber optic assembly 27 is insertable into, and removable from, the fixed sleeve 60 of the housing 26. Similarly, a second ferrule 62 of the fiber optic assembly 27 is insertable into, and removable from, the fixed sleeve 58 of the housing 26.

The ferrule 62 has fixed thereto a collection fiber 64 which is housed in the protective shielding 46, alongside the excitation fiber 44. A distal end 66 of the collection fiber 64 is held in the probe head 50.

A collimating lens 68 is aligned with the collection fiber ferrule 62 and directs Raman signal light 70 through the notch filter 34 and into the spectrometer 22, and in particular the light analyzer LA.

While a specific arrangement of light manipulating devices 28 has been shown and described, it will be apparent that any suitable arrangement of light manipulating devices could be used to direct excitation laser light therethrough to the excitation fiber and to receive Raman signal light by way of the collection fiber 64 and direct the Raman signal light to the light analyzer of the spectrometer.

If, in use, any part of the fiber optic assembly 27, such as the probe head 50 and/or protective shielding 46 becomes contaminated, the ferrules 32, 62 may simply be "unplugged" from the sleeves 60, 58, and replaced with another optical fiber assembly, including a new probe head.

Both the fiber optic assembly, and the interface module can be readily removed from the spectrometer. Any selected releasable mechanical connection means can be used to attach the interface module to the spectrometer, including snap-on, clamp-on, screw-on, slide-and-lock-on arrangements, and the like.

Figure 3:
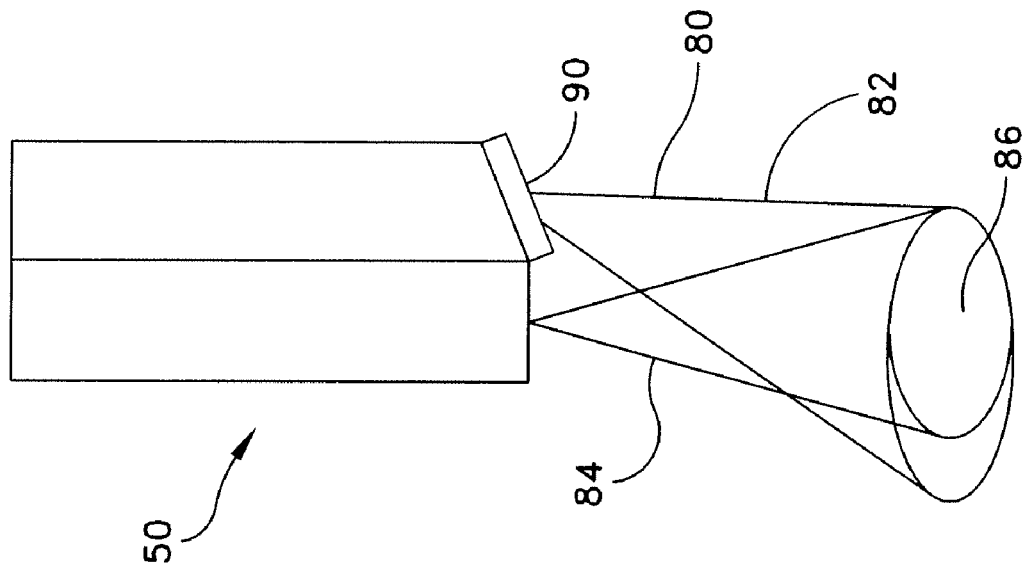
FIG. 3 is a side elevational of the probe head portion of FIG. 2.
Figure 2:
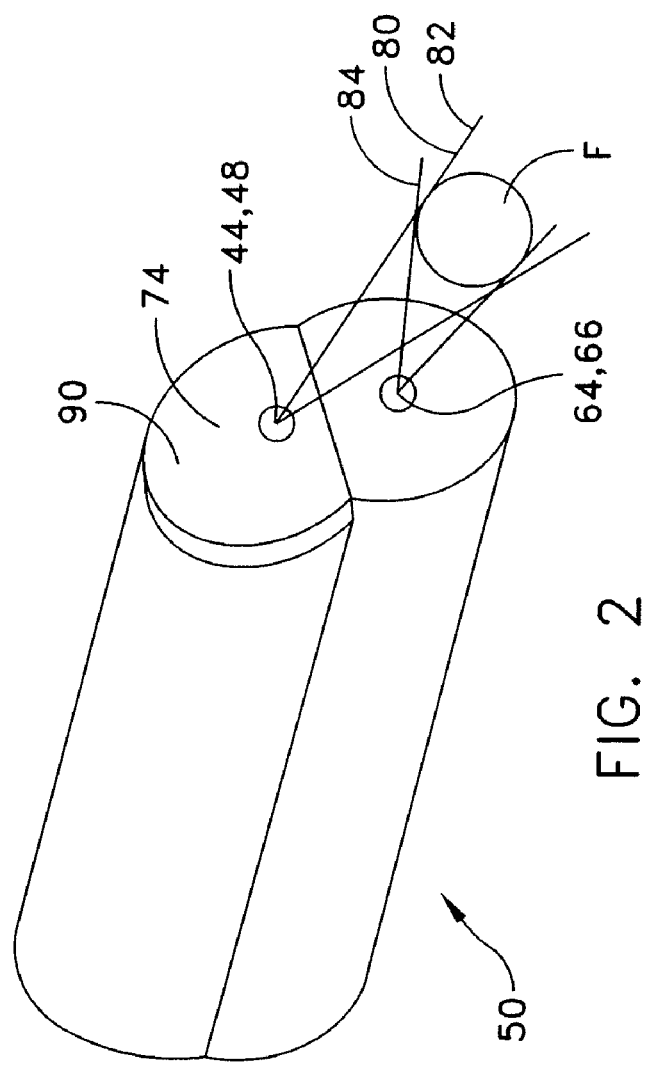
FIG. 2 is a diagrammatic perspective view of a probe head portion of a fiber optic assembly of FIG. 1.

Referring to FIGS. 2 and 3, it will be seen that the probe head 50 may be shaped such that the geometry of the area of the specimen S which is impacted can be predetermined. As shown in FIGS. 1 and 2, an end facet 74 of the excitation fiber 44 can be at an angle to the end 66 of the collection fiber 64.

As shown in FIGS. 2 and 3, the laser light 80 emitted from the distal end 48 of the excitation fiber 44 is in a cone configuration 82. Light reflected from the specimen S, that is, the Raman signal light 70, travels back in a cone-shaped path 84 towards the distal end 66 of the collection fiber 64 and also disperses outwardly from the path 84 and is lost. The amount of collected Raman signal depends in large measure on the geometry of the design of the probe head 50 and particularly on the cone overlap area 86 effected by the two fibers 44, 64.

Figure 4:
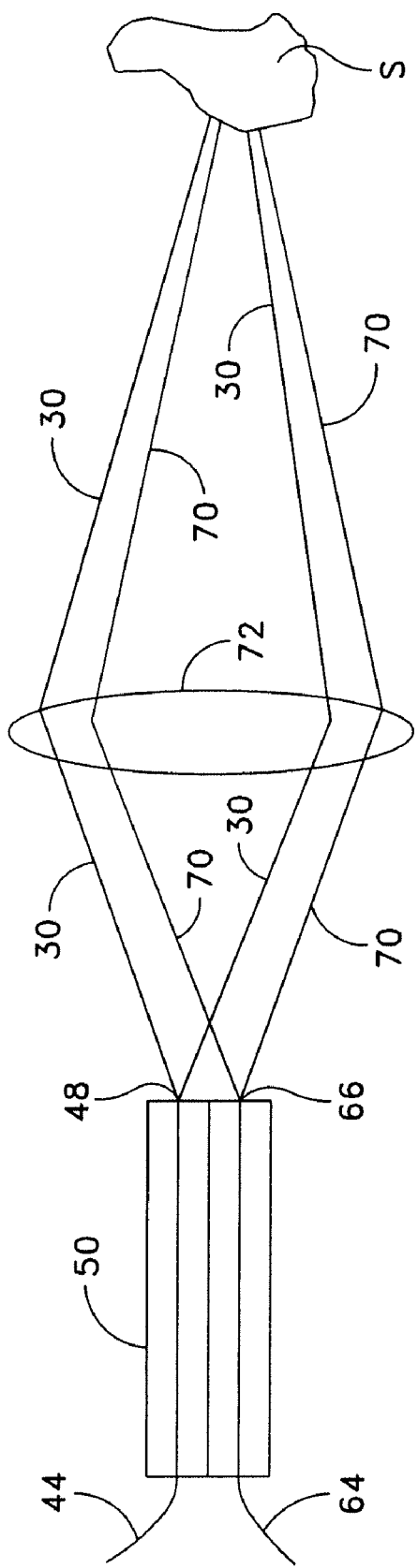
FIG. 4 is a schematic illustration of a further portion of the spectrometry assembly of FIG. 1.

Referring to FIG. 4, it will be seen that the fiber optic assembly may include a lens 72 disposed adjacent the probe head distally of the distal ends of the excitation fiber 44 and the collection fiber 64. Alternatively, the lens 72 may be used as a separate component spaced from the probe head 50. Emerging from the distal end 48 of the excitation fiber 44, the laser light 30 diverges. The lens 72 focuses the light 30 on a small area of the specimen S under test. The reflected Raman signature light 70 similarly diverges, but is focused by the lens 72 onto the distal end 66 of the collection fiber 64. Thus, relatively little Raman signal is lost compared to the extensive loss realized in the arrangement shown in FIG. 2.

Referring again to FIGS. 1-3, it will be seen that the distal end 48 of the excitation fiber 44 may be covered with a thin fiber band pass filter 90 which transmits only laser light and rejects Raman signals which may be generated by the excitation fiber. Thus, the Raman signal light 70 includes substantially only Raman signal from the specimen S and essentially none from the excitation fiber.

Figure 5:
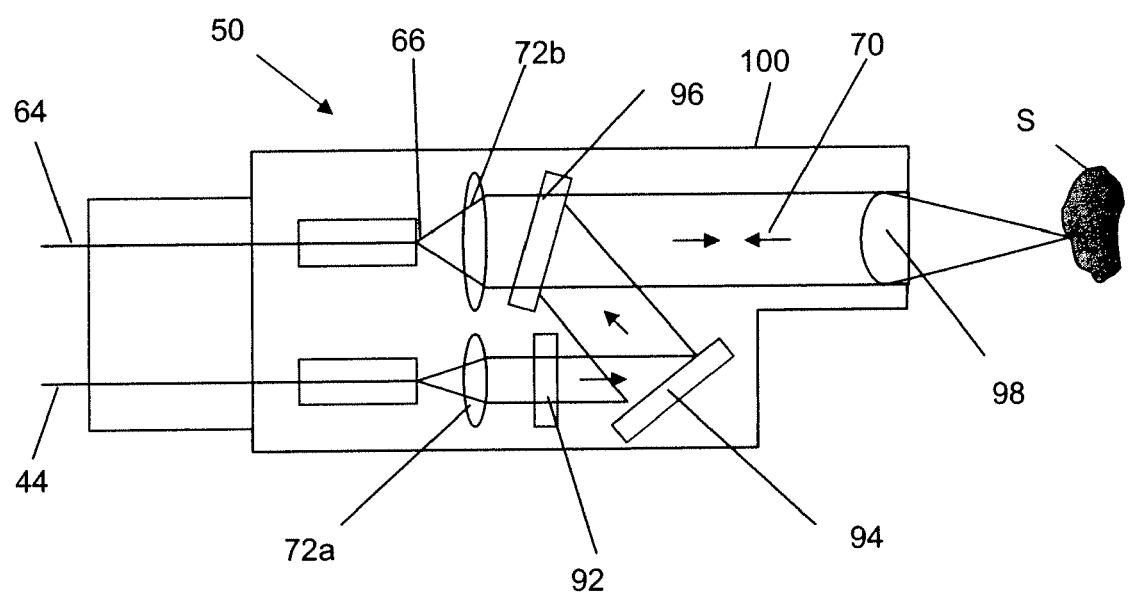
FIG. 5 is a schematic illustration of an alternative embodiment of the probe head portion.

Referring to FIG. 5, it will be seen that in an alternative embodiment, the fiber optic assembly probe head 50 includes first and second lenses 72a and 72b aligned distally of distal ends of the optical fibers 44, 64, the first 72a of the lenses being adapted to intercept diverging laser light emanating from the excitation fiber 44 and collimate the laser, and the second 72b of the lenses being adapted to intercept a Raman signal light 70 reflected from the specimen S and focus the Raman signal light onto the distal end 66 of the collection fiber 64. A band pass filter 92 is adapted to suppress Raman signal generated by the excitation fiber material and prevent such signal from reaching the specimen. A reflector 94 redirects the filtered laser light to a notch filter 96. The notch filter 96 is disposed in the probe head and is adapted to transmit Raman signal light emanating from the specimen and to block laser light reflected back from the specimen from reaching the distal end 66 of the collection fiber 64. A focusing lens 98 is disposed at the distal end of the probe head 50, the focusing lens 98 being adapted to focus the laser light on a reduced area of the specimen S, and further adapted to collect Raman signal light generated and reflected from the sample, and direct the reflected light toward the distal end 66 of the collection fiber 64. A water-sealed enclosure 100, made of a selected one of metal, plastic, ceramic material and any chemically inert material, serves to house components of the probe head 50.

There is thus provided a spectrometer assembly comprising a spectrometer, an interface module, and a fiber optic assembly, each connectable to and disconnectable from another. In the event of contamination or damage to the fiber optic assembly, it can be easily withdrawn from the interface module and replaced. The interface module may similarly be separated from the spectrometer and the probe head assembly and replaced with a module containing a different arrangement of light manipulation devices.

There is further provided a fiber optic assembly in which the probe head projects substantially only laser light, not mixed with Raman signature light.

There is still further provided a fiber optic assembly having, or in combination with, a lens which accepts diverging laser light exiting an excitation fiber and focuses the laser light on a limited area of a specimen under test, and which accepts diverging Raman signal light from the specimen and focuses the Raman light on a distal end of a collection fiber.

The above-described assembly may be used to obtain a Raman analysis in accordance with a method including the steps of providing the Raman spectrometer 22 having the laser light source and the Raman signal analyzer, providing the interface module 24 which is adapted for attachment to the spectrometer 22, the module 24 having therein light manipulating devices 28 for directing laser light and Raman signal light for effecting excitation of the specimen and collection and directing of Raman signal light to the Raman signal analyzer, and providing the fiber optic assembly 27 comprising the excitation fiber 44, the collection fiber 64, and the probe head 50, attaching the interface module 24 to the spectrometer 22, attaching the fiber optic assembly to the interface module 24, placing the probe head 50 adjacent the specimen S, and energizing the laser light source LS, whereby to cause laser light to pass from the spectrometer 22 to the interface module 24 and therein to be directed by the light manipulating devices 28 to the excitation fiber 44 and the probe head 50 and onto the specimen S, and thence Raman signal light back through the collection fiber 64 to the interface module 24 wherein the manipulating devices 28 direct the Raman signal light to the spectrometer Raman light analyzer LA.

The method preferably includes the further step of providing the focusing lens 72 between the fiber distal ends 48, 66 and the specimen S, such that Raman signal light from the specimen is focused on the distal end 66 of the collection fiber 64.

It is to be understood that the present invention is by no means limited to the particular construction and method steps disclosed and/or shown in the drawings, but also comprises any modification or equivalent within the scope of the claims.

What is claimed is:

1. A Raman spectrometry assembly comprising:
   a Raman spectrometer comprising a laser light source and a Raman signal analyzer, the laser light source providing laser light to a port and the Raman signal analyzer receiving Raman signal light from the port;
   an interface module comprising a housing which is connectable to and disconnectable from said spectrometer, the interface module provided with first and second openings, the interface module provided with light manipulators adapted to direct laser light received from the port to the first opening and to direct Raman signal light received from the second opening to the port; and
   a fiber optic assembly which is connected to said interface module, said fiber optic assembly comprising a probe head portion at a distal end thereof for disposition adjacent a specimen to be tested, and optical fibers extending from said probe head portion and adapted to extend to said interface module.

2. The spectrometry assembly in accordance with claim 1 wherein each of said optical fibers is provided with a ferrule fixed to a proximal end of the fiber.

3. The spectrometry assembly in accordance with claim 2 wherein the first and second openings; are each for receiving one of the ferrules.

4. The spectrometry assembly of claim 1, wherein said fiber optic assembly comprises an elongated excitation fiber having a proximal end for receiving the laser light from said interface module, and a distal end for emitting the laser light onto the specimen, and an elongated collection fiber having a distal end for receiving the Raman signal light from the specimen, and a proximal end for emitting the Raman signal light into said interface module.

5. The spectrometry assembly of claim 4, wherein the light manipulators are configured to direct the laser light from the port to said excitation fiber and for directing the Raman signal light from said collection fiber to the port.

6. The spectrometry assembly in accordance with claim 5 wherein the light manipulators comprise a notch filter for receiving laser light from said laser light source and directing the laser light to a reflector which reflects the laser light to a focusing lens, the focusing lens being adapted to focus the laser light onto a ferrule fixed to a proximal end of the excitation fiber, and a second focusing lens for receiving the Raman signal light from the collection fiber and directing the receiving Raman signal light to said Raman light analyzer.

7. The Raman spectrometry assembly of claim 1 comprising:
   first and second sleeves disposed in the first and second openings, respectively;
   wherein the fiber optic assembly comprises first and second ferrules adapted for insertion into and withdrawal from said sleeves, an elongated excitation fiber fixed to and extending from said first ferrule, and an elongated collection fiber fixed to and extending from said second ferrule, distal ends of said fibers being fixed to a probe head; and
   wherein said ferrules are readily withdrawable from said sleeves and replaceable by other ferrules.

8. The Raman spectrometry assembly in accordance with claim 7 wherein said ferrules are adapted for slidable insertion into and withdrawal from said sleeves.

9. The Raman spectrometry assembly in accordance with claim 7 wherein the first and second openings are disposed side-by-side in the same wall of said housing.

10. The Raman spectrometry assembly in accordance with claim 7 wherein said sleeves are each provided with a flange secured to the wall of said housing.

11. A Raman spectrometry assembly comprising:
    a Raman spectrometer comprising a laser light source and a Raman signal analyzer;
    an interface module adapted for connection to and disconnection from said spectrometer, and having a first opening extending through a wall thereof;
    light manipulating components disposed in said interface module for directing a laser beam emitted from said laser light source of said spectrometer toward the first opening:

a first focusing lens mounted in said interface module and aligned with the first opening;

a first sleeve disposed in the first opening;

a fiber optic assembly comprising a first ferrule adapted for insertion into said first sleeve and adapted for removal therefrom, said first ferrule being further adapted to reside in said first sleeve and therein to receive and transmit the laser light emitted from said laser light source and laser light directing components to an excitation fiber proximal end fixed to said first ferrule, an elongated excitation fiber extending from the proximal end thereof to a distal end thereof fixed in a probe head, a collection fiber extending from the probe head to a second ferrule removably disposed in a second sleeve disposed in a second opening in said interface module; and a second focusing lens mounted in the interface module and aligned with the second opening and adapted to pass collection fiber light therethrough and through a portion of said light directing components to the Raman signal analyzer of said spectrometer; wherein said first ferrule and the second ferrule are removable from said first sleeve and the second sleeve, and said first sleeve and the second sleeve are adapted to receive further ferrules of a configuration substantially identical in size and shape to said first ferrule and the second ferrule, wherein the fiber optic assembly may readily be replaced by another fiber optic assembly.

12. The Raman spectrometry assembly in accordance with claim 11 wherein the ferrules are adapted for slidable insertion into and withdrawal from said sleeves.

13. The Raman spectrometry assembly in accordance with claim 11 wherein the first and second openings are disposed side-by-side in the same wall of said interface module.

14. The Raman spectrometry assembly in accordance with claim 13 wherein the sleeves are each provided with a flange secured to the same wall of said interface module.

15. A Raman spectrometry assembly comprising:
a Raman spectrometer comprising a laser light source and a Raman signal analyzer;
an interface module adapted to pass laser light therethrough and into a flexible excitation fiber connected to said module, and adapted to pass Raman signal light from a flexible collection fiber connected to said module therethrough to the Raman signal analyzer; and
a fiber optic assembly comprising a flexible elongated protective shielding disposed around the excitation fiber and the collection fiber, and a probe head wherein distal ends of the excitation fiber and collection fiber are mounted, the excitation fiber distal end being adapted to direct laser light onto a specimen, and the collection fiber distal end being adapted to receive Raman signature light from the specimen;
wherein said distal end of said excitation fiber is covered with a band pass filter to block flow of Raman signal light therethrough, such that laser light emitted by said distal end of said excitation fiber is substantially devoid of Raman signal light.

16. The Raman spectrometry assembly in accordance with claim 15 wherein said fiber optic assembly further comprises a focusing lens adjacent the distal ends of the excitation fiber and the collection fiber, and wherein the laser light emitted by the excitation fiber passes through said focusing lens which focuses the laser light onto a small portion of the specimen, and wherein the Raman signal light from the specimen passes through said focusing lens which focuses the Raman signal light onto the distal end of said collection fiber.

17. A Raman spectrometry assembly comprising:
a Raman spectrometer comprising a laser light source and a Raman signal analyzer;
an interface module; and
a fiber optic assembly connectable to and disconnectable from said interface module, the fiber optic assembly comprising a probe head at a distal end thereof for disposition adjacent a specimen to be tested, and optical fibers extending from said probe head and adapted to extend to said interface module, said optical fibers including an excitation fiber for transmitting laser light from said interface module to a specimen under test, and a collection fiber for transmitting Raman signal light from the specimen to the interface module; and
a lens aligned distally of distal ends of said optical fibers, said lens being adapted to intercept diverging laser light emanating from said excitation fiber and focus the light on a reduced area of the specimen, and to intercept a Raman signal light reflected from the specimen and focus the Raman signal light onto the distal end of said collection fiber.

18. The Raman spectrometry assembly in accordance with claim 17 wherein said lens is spaced from said probe head.

19. The Raman spectrometry assembly in accordance with claim 17 wherein said lens is disposed in said probe head.

20. A method for obtaining an analysis of a specimen, the method comprising the steps of:
providing a Raman spectrometer having a laser light source and a Raman signal analyzer;
providing an interface module which is adapted for attachment to the spectrometer, the module having therein light manipulating device for directing laser light and Raman signal light for effecting excitation of the specimen and collection and direction of Raman signal light to the Raman signal analyzer; and
providing a fiber optic assembly comprising an excitation fiber, a collection fiber, and a probe head;
attaching the interface module to the spectrometer;
attaching the fiber optic assembly to the interface module;
placing the probe head adjacent the specimen; and energizing the laser light source; whereby to cause laser light to pass from the spectrometer to the interface module and therein to be directed by the light manipulating devices to the excitation fiber and the probe head and onto the specimen, and thence to pass Raman signal light back through the collection fiber to the interface module wherein the manipulating devices direct the Raman signal light to said spectrometer Raman light analyzer;
providing a focusing lens between the fiber distal ends and the specimen, such that excitation light is focused on the specimen, such that excitation light is focused on the specimen, and Raman signal light from the specimen is focused on the distal end of the collection fiber.

21. A Raman spectrometry assembly comprising:
a Raman spectrometer comprising a laser light source and a Raman signal analyzer;
an interface module; an
a fiber optic assembly connectable to and disconnectable from said interface module, said fiber optic assembly comprising a probe head at a distal end thereof for disposition adjacent a specimen to be tested, and optical fibers extending from said probe head and adapted to extend to said interface module, said optical fibers comprising and excitation fiber for transmitting laser light from said interface module to a specimen under test, and a collection fiber for transmitting Raman signal light from the specimen to said interface module; and first and second lenses aligned distally of distal ends of said optical fibers, the first of said lenses being adapted to intercept diverging laser light emanating from said excitation fiber and collimate the laser, and the second of said lenses being adapted to intercept a Raman signal light reflected from the specimen and focus the Raman signal light onto a distal end of said collection fiber;

and a band pass filter adapted to suppress Raman signal generated by excitation fiber material and prevent such signal from reaching the specimen;

a reflector for redirecting filtered laser light to a notch filter;

wherein the notch filter is disposed in said probe head and is adapted to transmit Raman signal light emanating from the specimen and to block laser light reflected back from the specimen from reaching the distal end of the collection fiber; and a focusing lens disposed at the distal end of said probe head, said focusing lens being adapted to focus the laser light on a reduced area of the specimen, and further adapted to collect Raman signal light generated and reflected from the sample and direct the reflected light toward the distal end of said collection fiber; and a water-sealed enclosure made of a selected one of metal, plastic, ceramic material and any chemically inert material, to house components of said probe head.

22. The Raman spectrometry assembly in accordance with claim 21 wherein said focusing lens is configured to be removable from said probe head.

23. The Raman spectrometry assembly in accordance with claim 21 wherein said focusing lens is disposed in said probe head.

* * * * *

UNITED STATES PATENT AND TRADEMARK OFFICE
CERTIFICATE OF CORRECTION

PATENT NO. : 7,701,571 B2  Page 1 of 1
APPLICATION NO. : 11/894887
DATED : April 20, 2010
INVENTOR(S) : Masud Azimi et al.

It is certified that error appears in the above-identified patent and that said Letters Patent is hereby corrected as shown below:

At column 8, line 13, delete "openings;" and insert -- openings --.

At column 8, line 67, delete "opening:" and insert -- opening; --.

At column 10, line 57, after "module;" delete "an" and insert -- and --.

At column 10, line 64, delete "and" and insert -- an --.

Signed and Sealed this

Thirteenth Day of July, 2010

David J. Kappos
*Director of the United States Patent and Trademark Office*